Feb. 16, 1954 E. S. BOERNER Plant Pat. 1,253

ROSE PLANT

Filed Feb. 24, 1953

Inventor
E. S. Boerner
By: Robert Todd
Attorney

Patented Feb. 16, 1954 Plant Pat. 1,253

UNITED STATES PATENT OFFICE 1,253

ROSE PLANT

Eugene S. Boerner, Newark, N. Y., assignor to Jackson & Perkins Company, Newark, N. Y., a corporation of New York Application February 24, 1953, Serial No. 338,630

1 Claim. (Cl. 47—61)

The present invention relates to a new and distinct variety of rose plant of the climber class, which was originated by me by crossing an unnamed and unpatented climbing seedling of "New Dawn" (Plant Patent No. 1) with the variety "Climbing World's Fair" (Plant Patent No. 546).

The primary objective of this cross was to obtain a new remontant and recurrent climber, combined with an improvement in the form and color of the variety "New Dawn." This objective was fully achieved, as evidenced by the fact that the new variety is very free in its first blooming, as well as throughout the remainder of the growing season; it is endowed with a vigorous habit of growth; it is unusually hardy for such a large-flowered climbing remontant rose; and its blooms have very good form and are of an improved color which may be described as Rose Red in general color tonality.

Asexual reproduction of the new variety by budding at Newark, New York, and also at Pleasanton, California, shows that the foregoing characteristics and distinctions come true to form and are established and transmitted through succeeding propagations.

Figure 3:
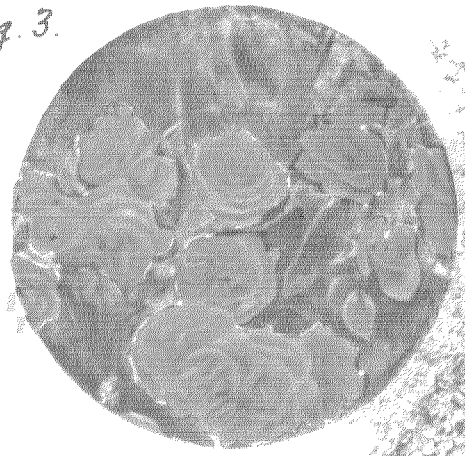
Fig. 3 is a somewhat enlarged view, in color, of typical specimen blooms and foliage in different stages of development.
Figure 2:
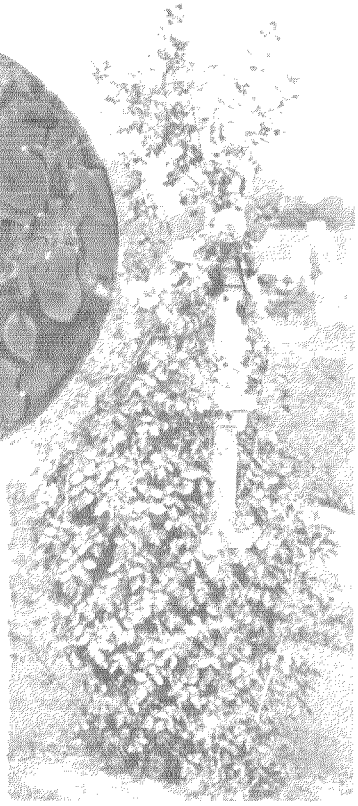
Fig. 2 is another view in black-and-white of a typical specimen plant of the new variety which has attained substantial growth during the growing season (approximately 8 feet), thus illustrating the climbing habit and the freedom of bloom on the ends of the growth.
Figure 1:
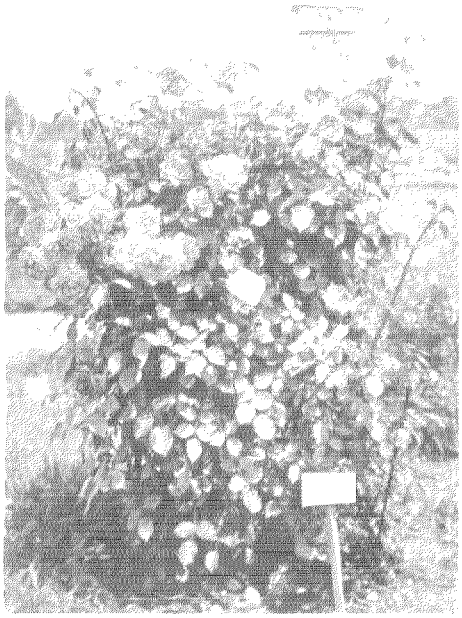
Fig. 1 is a view in black-and-white, showing a typical specimen plant of the new variety and illustrating its exceptional freedom of bloom at its first-blooming stage.

The following is a detailed description of the new variety, with color terminology in accordance with Ridgway's Color Standards and Nomenclature:

Parentage: Seedling.
- *Seed parent.*—An unnamed climbing seedling of "New Dawn."
- *Pollen parent.*—"Climbing World's Fair."

Classification:
- *Botanic.*—Climber.
- *Commercial.*—Climber.

*Flower*

(Observations made in a field at Newark, New York, near the middle of the month of August.)

Blooming habit: Recurrent; continuous.

Bud:
- *Size.*—Medium.
- *Form.*—Ovoid; is not affected by wet or hot weather.
- *Color.*—When sepals first divide—Tyrian Rose, Plate 12. When petals begin to unfurl—Rose Red, Plate 12. When half blown: inside of petals—Tyrian Rose, Plate 12; reverse of petals—Rose Red, Plate 12.
- *Sepals.*—Smooth edge and slightly branched; curl back when petals being to unfurl. Color: inside—Kildare Green, Plate 31; outside—Absinthe Green, Plate 31.
- *Calyx.*—Color—Absinthe Green, Plate 31. Shape — pear. Size — small. Aspect — smooth. Odor when rubbed—none.
- *Peduncle.* — Length — medium. Aspect — rough. Color—Absinthe Green, Plate 31. Strength—erect; slender.
- *Opening.*—Does open up well; is not affected by adverse weather conditions.

Bloom:
- *Size.*—Large; average size when fully expanded—3½ inches to 4 inches.
- *Borne.*—Singly and several together.
- *Stems.*—Long; normal strength.
- *Form.*—When first open—cupped. Permanence—retains its form to the end.
- *Petalage.*—Double (full but open center). Number of petals under normal conditions—30 to 35.
- *Color.*—Center of flower—Rose Red, Plate 12. Outer petals—Rose Color, Plate 12. Base of petals (aiglet)—Pale Green Yellow, Plate 5. Inside of petals—Rose Red, Plate 12; lower half of the petal extending from the base lightly overcast with Rose Color, Plate 12. Reverse of petals—Rose Color, Plate 12, slightly overcast with Rose Red, Plate 12. General tonality from a distance—Rose Red, Plate 12.
- *Discoloration.*—General tonality at end of first day—Rose Red, Plate 12. Second day—Rose Red, Plate 12, lightly overcast with Rose Color, Plate 12. Third day—Rose Color, Plate 12, lightly overcast with Rose Red, Plate 12.

Petals:
- *Texture.*—Thin; is not affected by wet or hot weather.
- *Appearance.* — Inside — satiny; outside — shiny.
- *Form.*—Oval.

*Arrangement.*—Imbricated (regularly arranged shingle-like).
*Petaloids in center.*—Few; small.
*Persistence.*—Drop off cleanly.
*Fragrance.*—Moderate. Nature—Tea (average hybrid tea scent).
*Lasting quality.*—On the plant—long.

*Genital organs*

Stamens, anthers: Medium size; few.
*Color.*—Warm Buff, Plate 15.
*Arrangement.*—Regular around styles.
Stamens, filaments (threads): Medium length. Color—Eosine Pink, Plate 1.
Pollen: Color—Light Buff, Plate 15.
Styles: Loosely separated; uneven length; medium length; thin.
Stigmas: Color—Seafoam Yellow, Plate 31.
Ovaries: All enclosed in calyx.
Seeds: None.

*Plant*

Form: Climber.
Growth: Vigorous; upright; branching; 8-foot shoots.
Foliage: 5 to 7 leaflets.
*Size.*—Medium.
*Quantity.*—Normal abundance.
*Color.*—New foliage: upper side—Yellowish Oil Green, Plate 5, lightly overcast with Carmine, Plate 1; serrations Carmine, Plate 1; under side—Oil Green, Plate 5, lightly overcast with Oxblood Red, Plate 1. Old foliage: upper side—Bice Green, Plate 17; under side—Light Bice Green, Plate 17.
*Shape.*—Oval pointed.

*Texture.*—Upper side—glossy. Under side—smooth. Ribs and veins—ordinary.
*Edge.*—Serrated (saw-toothed).
*Serration.*—Double and single; small.
*Leaf stem.*—Color—Biscay Green, Plate 17. Under side—prickles.
*Stipules.*—Medium length; smooth.

Wood:
*New wood.*—Color—Absinthe Green, Plate 31. Bark—smooth.
*Old wood.*—Color—Cress Green, Plate 31. Bark—smooth.

Thorns:
*Thorns.*—Quantity—on main stalks from base and on laterals from stalk—ordinary. Form—narrow base; medium length; straight. Color when young—Citrine, Plate 4. Position—irregular.
*Prickles.*—Quantity—on main stalks and on laterals—none.
*Short needles.*—Quantity—on main stalks and on laterals—none.

I claim:

A new and distinct variety of rose plant of the climber class, substantially as herein shown and described, characterized particularly as to novelty by its remontant and vigorous habits of growth, by its freedom of bloom in the early part of the growing season, as well as throughout the growing season thereafter, by its exceptional hardiness, and by the distinctive Rose Red general color tonality of its blooms.

EUGENE S. BOERNER.

No references cited.